(12) United States Patent
Kraushaar

(10) Patent No.: US 7,338,476 B2
(45) Date of Patent: Mar. 4, 2008

(54) IV ADMINISTRATION SET IDENTIFICATION SYSTEM

(76) Inventor: Timothy Y. Kraushaar, 115 4th St., Seal Beach, CA (US) 90704

( * ) Notice: Subject to any disclaimer, the term of this patent is extended or adjusted under 35 U.S.C. 154(b) by 184 days.

(21) Appl. No.: 11/198,947

(22) Filed: Aug. 8, 2005

(65) Prior Publication Data
US 2005/0267404 A1    Dec. 1, 2005

Related U.S. Application Data

(63) Continuation-in-part of application No. 10/883,904, filed on Jul. 2, 2004, which is a continuation-in-part of application No. 10/629,222, filed on Jul. 29, 2003, now abandoned, which is a continuation-in-part of application No. 09/971,179, filed on Oct. 4, 2001, now Pat. No. 6,613,012, which is a continuation-in-part of application No. 09/854,711, filed on May 14, 2001, now abandoned.

(51) Int. Cl.
*A61M 5/00*    (2006.01)
(52) U.S. Cl. ...................... 604/251; 604/523
(58) Field of Classification Search ........ 604/257–258, 604/261, 262, 80, 93.01; 283/81
See application file for complete search history.

(56) References Cited

U.S. PATENT DOCUMENTS

| | | | |
|---|---|---|---|
| 3,817,428 A | 6/1974 | Buckley | |
| 3,924,661 A | 12/1975 | Bornhoffer | |
| 4,654,026 A | 3/1987 | Underwood | |
| 4,795,429 A | 1/1989 | Feldstein | |
| 4,999,885 A | 3/1991 | Lee | |
| 5,046,609 A * | 9/1991 | Mangini et al. | 206/232 |
| 5,078,699 A | 1/1992 | Haber et al. | |
| 5,169,385 A | 12/1992 | Turnbull | |
| 5,180,504 A | 1/1993 | Johnson et al. | |
| 5,224,932 A | 7/1993 | Lappas | |
| 5,338,314 A | 8/1994 | Ryan | |
| 5,423,750 A | 6/1995 | Spiller | |
| 5,439,448 A | 8/1995 | Leschinsky et al. | |
| 5,642,906 A * | 7/1997 | Foote et al. | 283/67 |
| 5,657,874 A | 8/1997 | Hustad et al. | |
| 5,958,536 A * | 9/1999 | Gelsinger et al. | 428/40.1 |

(Continued)

FOREIGN PATENT DOCUMENTS

DE    297 20 382 U1    11/1997

*Primary Examiner*—LoAn H Thanh
(74) *Attorney, Agent, or Firm*—Klein, O'Neill & Singh, LLP; Howard J. Klein

(57) ABSTRACT

An IV administration set identification kit includes identification elements for identifying an IV administration set having an IV solution container, a drip chamber, and an IV line including a Y-site or port. The identification elements are a first adhesive strip configured for attachment to the IV solution container, a second adhesive strip configured for attachment to the drip chamber, and a Y-site identification element configured for attachment to the Y-site, wherein the first and second adhesive strips and the Y-site identification element are marked with matching identification symbols. The first and second adhesive strips and the Y-site identification element are contained within a packet having an openable side. The packet may include a backing sheet to which the first and second adhesive strips are removably attached.

5 Claims, 7 Drawing Sheets

U.S. PATENT DOCUMENTS

| | | |
|---|---|---|
| 6,000,726 A | 12/1999 | Campbell |
| 6,261,267 B1 | 7/2001 | Chen |
| 6,338,798 B2 | 1/2002 | Hopkins et al. |
| 6,613,012 B2 | 9/2003 | Kraushaar |
| 6,955,002 B2 * | 10/2005 | Sandel et al. ................. 40/638 |
| 2002/0056989 A1 * | 5/2002 | Lewis-Leander ............. 283/81 |

* cited by examiner

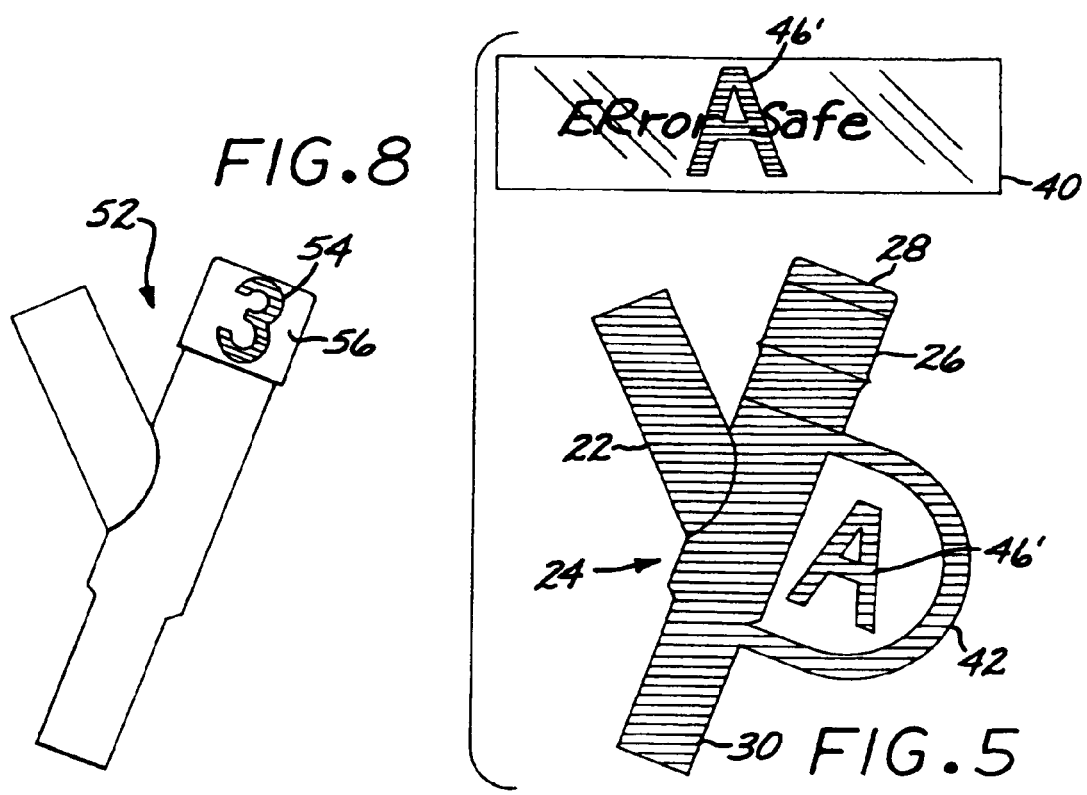
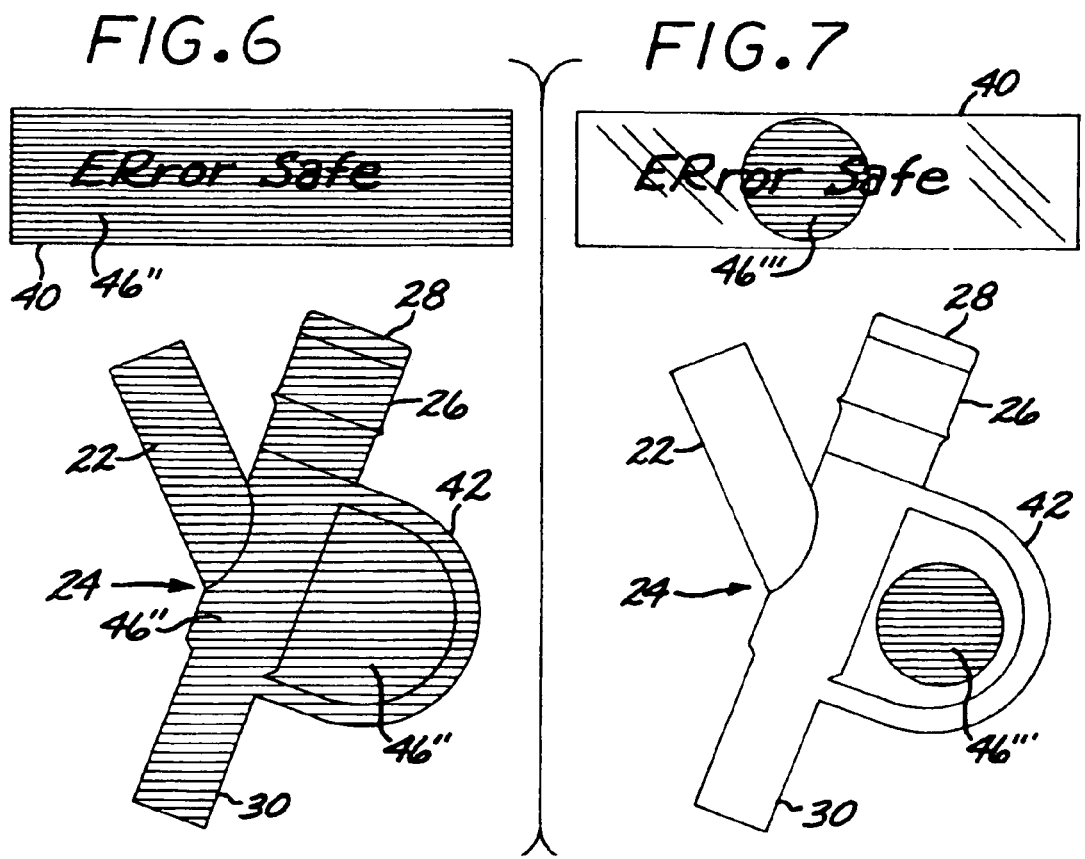

FIG. 9
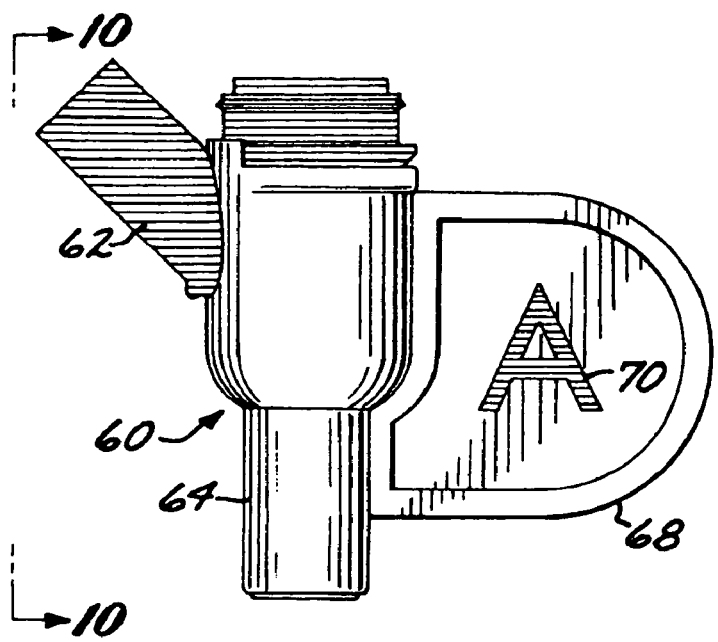
FIG. 10
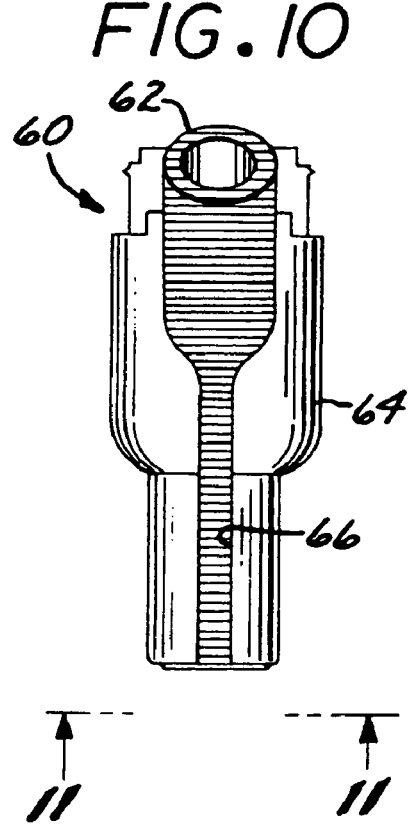
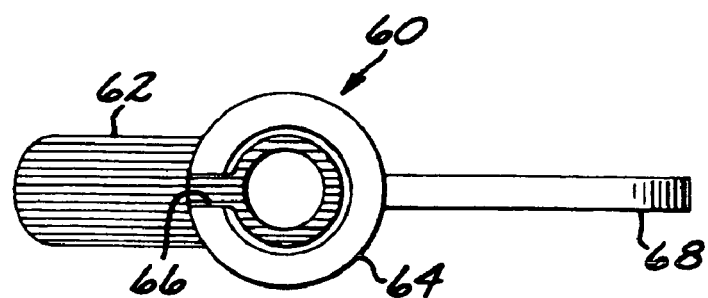
FIG. 11

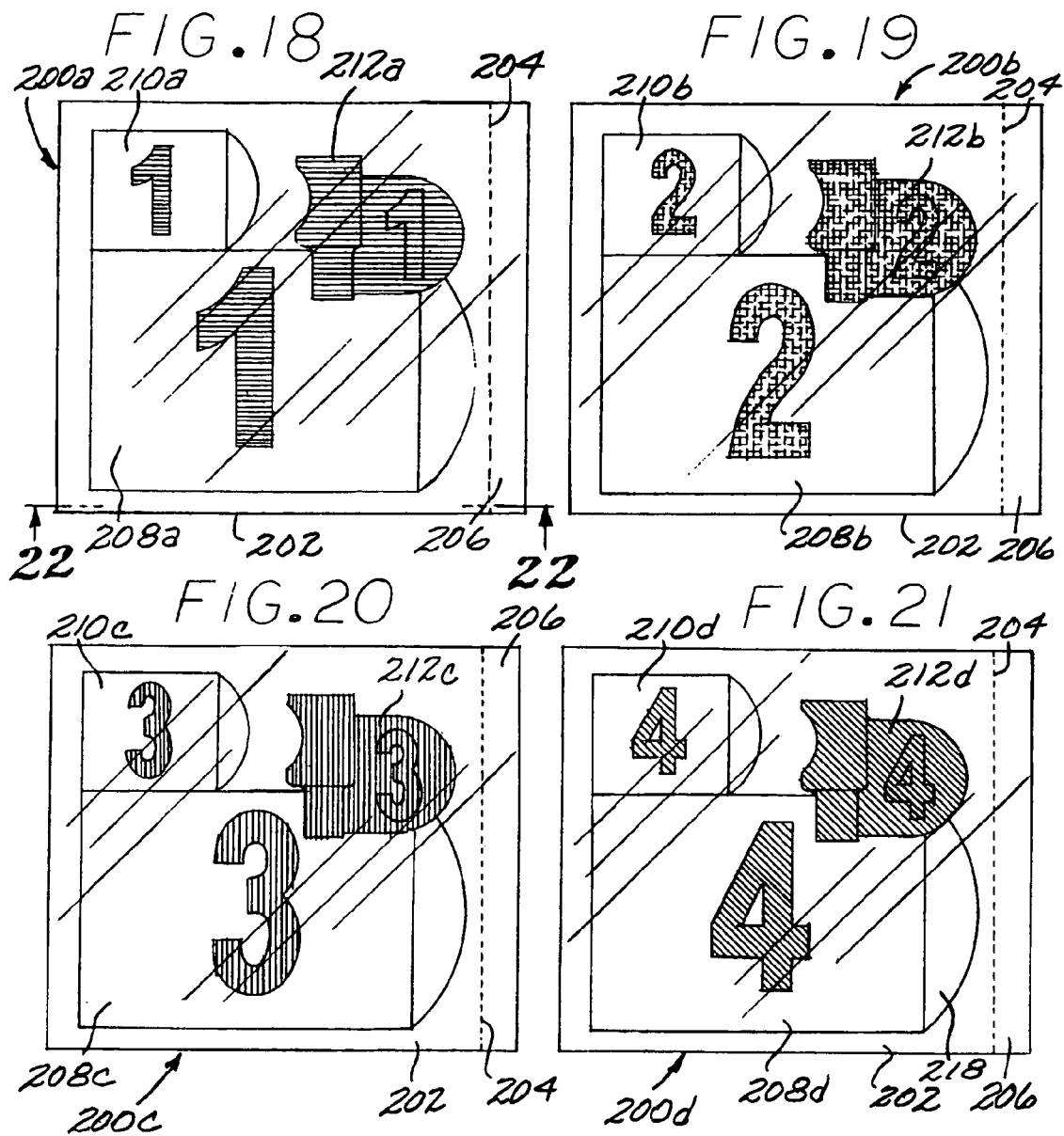
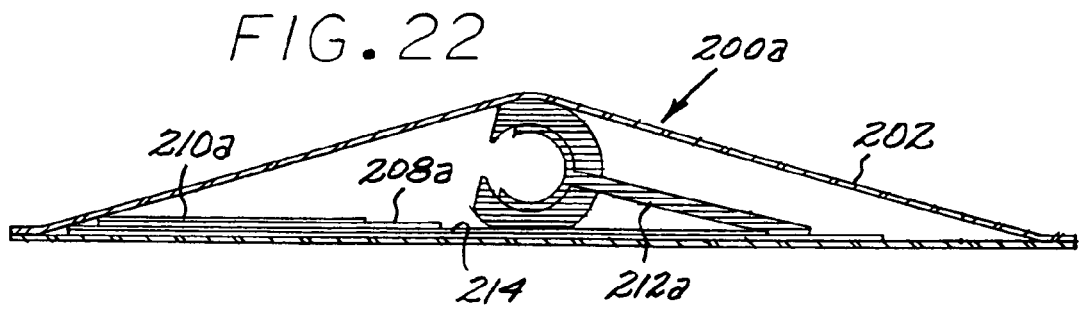

IV ADMINISTRATION SET IDENTIFICATION SYSTEM

CROSS-REFERENCE TO RELATED APPLICATIONS

This application is a Continuation-in-Part of application Ser. No. 10/883,904; filed Jul. 2, 2004; which is a Continuation-in-Part of application Ser. No. 10/629,222; filed Jul. 29, 2003, now abandoned; which is a Continuation-in-Part of application Ser. No. 09/971,179, filed Oct. 4, 2001, now U.S. Pat. No. 6,613,012; which is a Continuation-in-Part of application Ser. No. 09/854,711, filed May 14, 2001, now abandoned. The disclosures of these prior applications are incorporated herein by reference.

FEDERALLY-SPONSORED RESEARCH OR DEVELOPMENT

Not Applicable

BACKGROUND OF THE INVENTION

The present invention relates to a system for uniquely identifying each one of two or more intravenous (IV) lines that may be simultaneously employed to deliver drugs intravenously to one or more patients respectively from two or more containers (such as IV bags or bottles).

There are medical situations, such as emergency rooms, trauma centers, and wards, in which two or more patients are simultaneously receiving IV drugs. Also, a single hospital patient often requires the administration of multiple IV drugs delivered separately, but simultaneously, through two or more separate IV sets, at widely different dosage rates. In such situations, it is necessary to assure that each container of drug solution is properly matched to the correct IV line and from there to the correct patient. Confusion in matching these elements must be avoided to assure that each drug is administered in the proper dosage to the proper patient, lest a patient be injured through the administration of the wrong drug or an improper dose of the correct drug. Additionally, there have been numerous instances of contraindicated medications being introduced into an IV line at a "Y-site" or an in-line port, with possible endangerment of the patient. To date, efforts to avoid such confusion have largely been ad hoc. For example, medical personnel may attach numbered pieces of adhesive tape to IV containers and to IV lines to match them up properly. Still, a more reliable mechanism has been sought to achieve these ends.

SUMMARY OF THE INVENTION

Broadly, the present invention is a system for identifying IV administration set components, wherein the IV set includes an IV solution container, a drip chamber having a hollow spike for introduction into the container, and an IV line for delivering the IV solution to a patient, wherein the system comprises a first identification element that is removably attached to the drip chamber for subsequent attachment to the container; a second identification element permanently affixed to the drip chamber; and a third identification element attached to a Y-site or port in the IV line.

In specific preferred embodiments, the first identification element is a strip or patch that is adhesively attached to the drip chamber in a manner that will allow it to be removed therefrom for subsequent attachment to the IV solution container. The second identification element is a marker, preferably a strip or a patch, that is permanently affixed to the drip chamber. The third identification element is attached to a Y-site or port that is part of the IV line. The third identification element may be an integral part of the Y-site or port, or it may be removably attached to it. The first, second, and third identification elements bear matching identification symbols. In the context of this invention, the term "symbol" is deemed to encompass one or more letters, numbers, geometric shapes, abstract shapes, colors, and any combination of these elements. The term "symbol" may also include a color alone.

Viewed another way, the system of the invention comprises a matched set of plural identification elements bearing matching identification symbols, wherein a first one of the set is attachable to the IV solution container; a second one of the set is attached to the drip chamber; and a third one of the set is attached to the IV line remote from the first and second identification elements in the set. In practice, the system will advantageously include two or more such matched sets of identification elements, each set bearing a unique identification symbol. In the context of this invention, however, the term "system" is meant to encompass one or more such matched sets of identification elements.

In another aspect, the present invention is a kit or package containing a matched set of identification elements that can be attached to the components of an IV administration system, wherein package or kit includes a first identification element that is attachable to an IV solution container, a second identification element that is attachable to the drip chamber, and a third identification element that is attachable to the IV line at a Y-site or port. The first and second identification elements are preferably provided by first and second plastic strips or patches that are removably attached to a backing sheet while contained in the package. The third identification element is provided by a clip-on identifier that is attachable to a Y-site or port. The first, second, and third identification elements are advantageously removably attachable to their respective components, so that they may be re-used.

BRIEF DESCRIPTION OF THE DRAWINGS

FIGS. 5, 6, 7, and 8 are elevational views of identification elements showing alternative types of identification symbols;

FIG. 9 is a side elevational view of a third identification element that is removably attached to a Y-site or port, in accordance with a second embodiment of the invention;

FIG. 10 is a front elevational view of the third identification element of FIG. 9 and the Y-site or port to which it is removably attached, taken along line 10-10 of FIG. 9;

FIG. 11 is a bottom plan view of the third identification element of FIG. 9 and the Y-site or port to which it is removably attached, taken along line 11-11 of FIG. 10;

FIGS. 18-21 are plan views of an IV administration set identification kit comprising a plurality (e.g., four) IV identification element packets, each containing a matched set of three identification elements that are attachable to the components of an IV administration set, in accordance with another aspect of the present invention;

FIG. 22 is a cross-sectional view taken along line 22-22 of FIG. 18;

FIG. 23 is a plan view of a first identification element included in the packet of FIG. 18;

FIG. 24 is a plan view of a second identification element included in the packet of FIG. 18;

FIG. 25 is an elevational view of a third identification element included in the packet of FIG. 18, showing the third identification element attached to a Y-site or port of the type shown in FIG. 14; and FIG. 26 is a plan view of an IV administration set to which the identification elements shown in FIGS. 23, 24, and 25 have been attached.

DETAILED DESCRIPTION OF THE INVENTION

Figure 1:
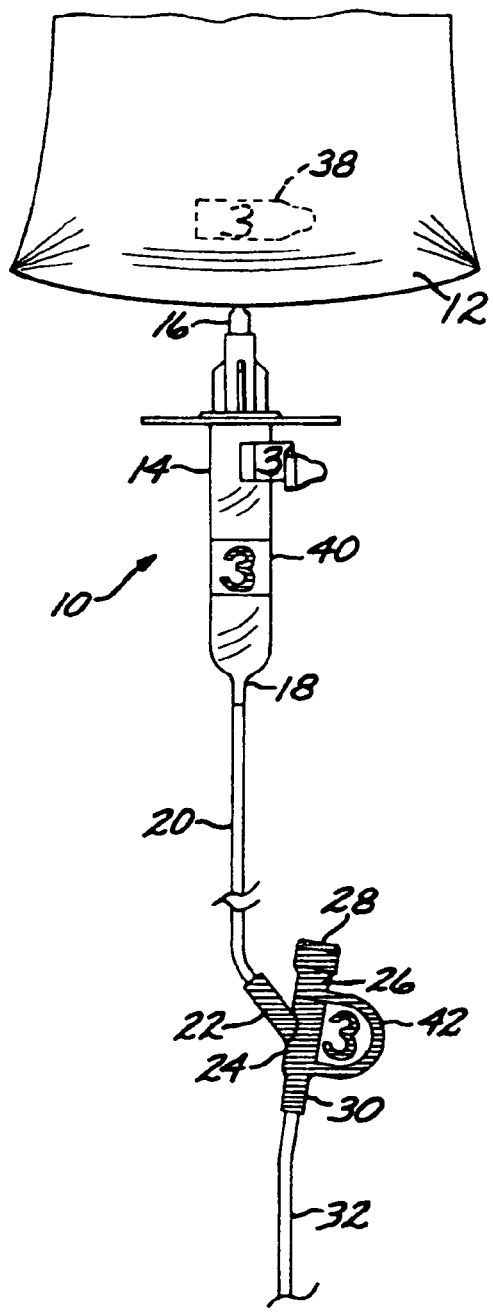
FIG. 1 is an elevation view of an IV administration set identification system in accordance with a first embodiment of the present invention, showing the system in use on a typical IV administration set.

Referring first to FIG. 1, a typical IV administration set 10 is shown, comprising a flexible plastic bag 12 serving as a container or reservoir for an IV drug solution (not shown). The set 10 also includes a drip chamber 14 having a hollow needle or spike 16 adapted to puncture the bag 12. The drip chamber 14 has an outlet 18 that communicates with a first segment 20 of a flexible IV line. The first IV line segment 20 has an outlet end that communicates with a first inlet branch 22 of a Y-shaped port or "Y-site" 24. The Y-site 24 is modified in accordance with the present invention, as will be described below. The Y-site 24 may advantageously have a second inlet branch 26 sealed by a puncturable septum 28. The septum 28 may be punctured by the needle of a syringe (not shown), or opened by a Luer connector or other device (not shown), for the administration of a supplemental drug into the IV line through the second inlet branch 26, as is well known in the art. The Y-site 24 has an outlet branch 30 that communicates with a second segment 32 of the flexible IV line, which terminates in an IV needle (not shown) that is adapted for insertion into a vein of a patient (not shown). Preferably, the outlet branch 30 is aligned axially with the second inlet branch 26, so as to form therewith a continuous tubular body.

Figure 4:
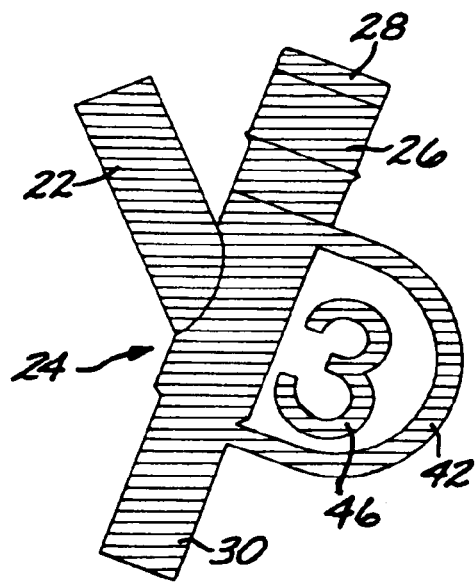
FIG. 4 is an elevational view of the third identification element of the IV set identification system shown in FIG. 1.
Figure 3:
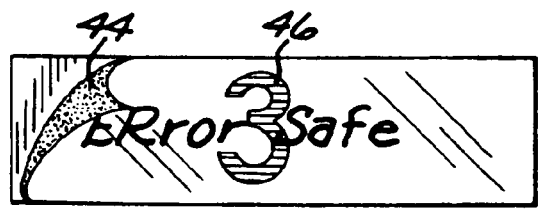
FIG. 3 is an elevational view of the second identification element of the IV set identification system shown in FIG. 1.

A first embodiment of the identification system of the present invention is shown in FIGS. 1, 2, 3, and 4. The system comprises a first identification element, in the form of a first adhesive patch or strip 38 (FIG. 2); a second identification element, preferably in the form of a second adhesive strip or patch 40 (FIG. 3); and third identification element, in the form of a flattened extension 42 that extends laterally or outwardly from the tubular body that comprises the second inlet branch 26 and the outlet branch 30 of the Y-site 24, and that is advantageously formed integrally therewith (FIG. 4).

Figure 2:
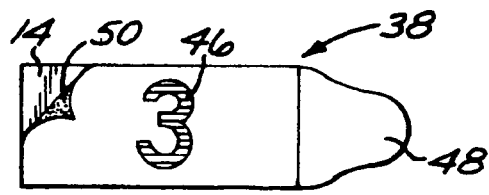
FIG. 2 is an elevational view of the first identification element of the IV set identification system used on the IV administration set of FIG. 1.

The first adhesive strip or patch 38 (FIG. 2) includes a pull tab 48 at one end and an adhesive backing 50 on its reverse side, but not on the back of the pull tab 48. The first adhesive strip or patch 38 is initially adhesively attached to the drip chamber 14 (as shown in FIG. 2 and in solid outline in FIG. 1). When the identification system of the present invention is used, however, the first adhesive strip or patch 38 is removed from the drip chamber 14 by means of the pull tab 48, and it is then adhesively applied to the exterior of the IV container 12, as shown in broken outline in FIG. 1.

The second adhesive strip or patch 40 also has an adhesive backing 44 (FIG. 3) that allows it to be fixed to the drip chamber 14 (as shown in FIG. 1). The adhesive backing 44 is advantageously such as to fix the second strip or patch 40 permanently to the drip chamber 14 as a permanent marker. Alternatively, the second identification element may simply be an identification symbol permanently marked on the drip chamber.

The first adhesive strip or patch 38, the second adhesive strip or patch 40, and the coupler extension 42 are each marked with a matching identification symbol 46. As shown in FIGS. 1, 2, 3, and 4, the symbol 46 may be a numeral. Preferably, color may be used as part of the identification symbols 46, whereby the symbols 46 have a matching color as well as a matching number. Still more preferably, the Y-site 24 may be made in the same color as the symbols 46.

In use, the identification system of the present invention will usually comprise two or more sets of identification elements, each set comprising a first strip or patch 38, a second strip or patch 40, and a Y-site 24 with an extension 42 bearing the same identification symbol 46, unique to that set.

FIGS. 5, 6, and 7 show alternative forms of the identification system, using different types of identification symbols. In FIG. 5 the symbol 46' is a letter, preferably in combination with a matching color. In FIG. 6 the symbol 46" is a color alone, the matching color being the predominant (if not sole) color of both the tab 42 and the strip 40. In FIG. 7 the symbol 46''' is a colored geometric shape. Still other types of symbols may be Roman numerals, abstract shapes and designs, and letters of non-Latin alphabets.

FIG. 8 illustrates an alternative form of the third identification element. In this form, the coupler or Y-site 52 is structurally an ordinary device of this type, lacking the extension 42 described above. The Y-site 52 is marked with an identification symbol 54 by means of a band 56 attached around the inlet branch of the coupler 52, the band 56 bearing the symbol 54. The band 56, which thus constitutes the third identification element, is preferably applied as a segment of shrink tubing, but it may also be in the form of an adhesive strip.

In use, the practitioner is provided with a drip chamber 14 to which the first identification element 38 is removably attached and the second identification element 40 is permanently fixed, and an IV line 20 having a Y-site or port 24 that includes the third identification element in the form of the integral extension 42 or the band 56. When an IV solution container 12 is selected, the drip chamber 14 is connected to the IV solution container 12 (by means of the hollow spike 16). The first identification element 38 is then removed from the drip chamber 14 and attached to the IV solution container 12. In this manner, a high degree of certainty is provided that the IV solution container is matched to the proper IV line.

FIGS. 9, 10, and 11 illustrate another embodiment of the invention, in which the third identification element is in the form of an attachment 60 that is removably attachable to a standard Y-site 62 having a first inlet branch 63*a* and a second inlet branch 63*b*. The attachment 60 comprises a sleeve 64 with an axial slit 66 and an integral lateral extension 68 that is marked with an identification symbol 70. The integral extension 68 is preferably located diametrically opposite the axial slit 66, and it is oriented substantially parallel to the slit 66. The sleeve 64 is made of a resilient, flexible, plastic material, and it is shaped and dimensioned to fit over and to conform to the exterior surface of the Y-site 62. The sleeve 64 can thus be slightly spread apart along the axial slit 66 to allow the second IV line 32 downstream from the Y-site 62 to be passed through the slit 66, and then the attachment 60 is pushed upwardly from the lower (downstream) end of the Y-site 62 until the Y-site 62 is received in the sleeve 64. The sleeve 64 is widened at its upper (upstream) end to accommodate the first inlet branch 63*a* of the Y-site 62. Likewise, the slit 66 is widened at its upper (upstream) end to accommodate the second inlet branch 63*b* of the Y-site 62. The attachment 60 may be removed by just reversing the aforementioned installation process. Alternatively, the attachment 60 can be installed snapping the sleeve 64 directly onto the Y-site 62 by spreading the sleeve 64 apart along the slit 66. Likewise, the sleeve 64 can be spread apart along the slit 66 for removal from the port or Y-site 62.

Figure 12:
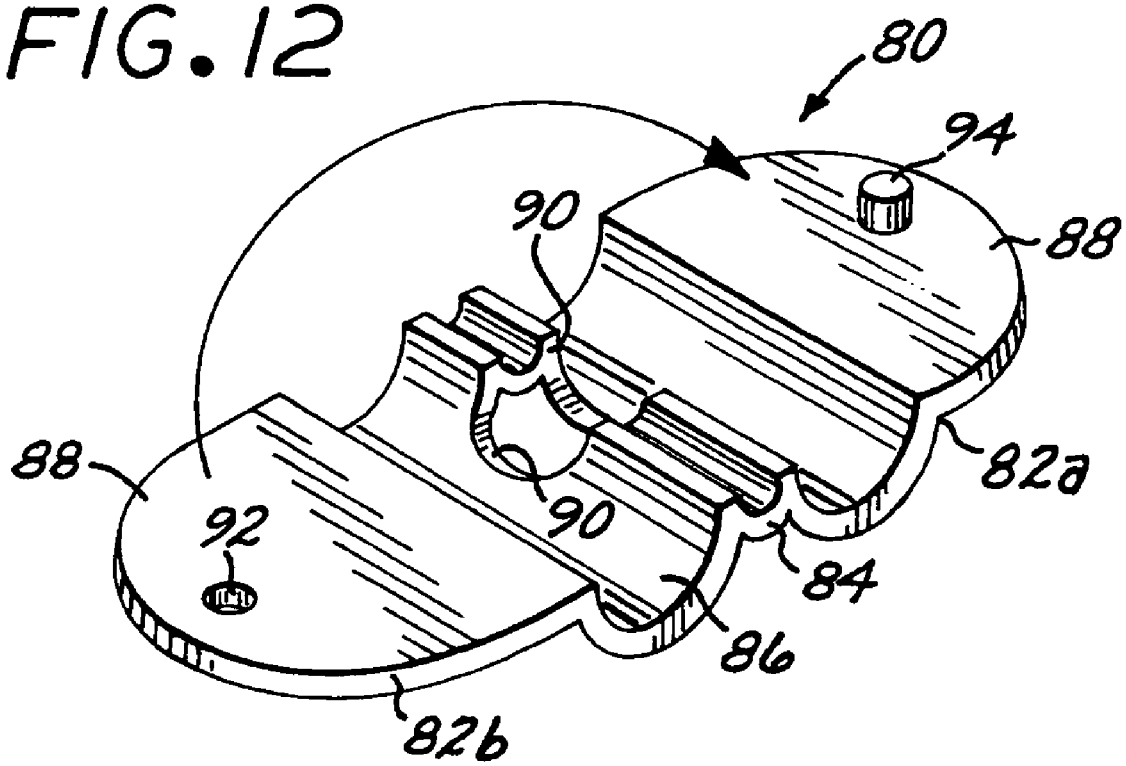
FIG. 12 is a perspective view of another form of the third identification element in accordance with the second embodiment of the invention, showing it in an open position.
Figure 13:
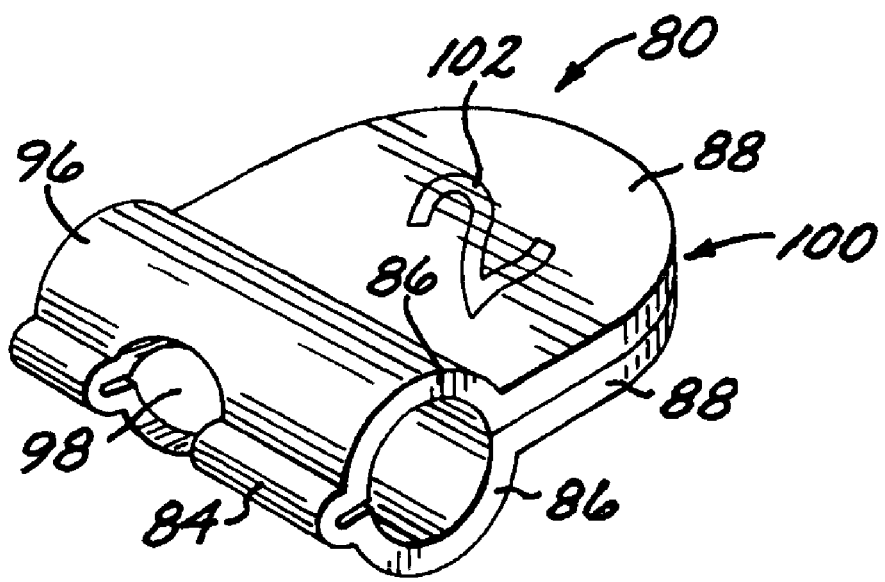
FIG. 13 is a perspective view of the third identification element of FIG. 12, showing it in a closed position.

FIGS. 12 and 13 illustrate another form of a snap-on attachment 80 that functions as the third identification element in the second embodiment of the invention. The attachment 80 comprises first and second mating sections 82*a*, 82*b*, respectively, joined by an integral hinge 84. Each of the sections comprises a trough-like portion 86, semicircular in cross-section, adjacent to, and aligned along, the hinge 84; and a flat, tabular portion 88 extending outwardly from the trough-like portion 86. Each of the trough-like portions 86 has a substantially semicircular cut-out 90 in the side adjoining the hinge 84. The tabular portion 88 of the first section 82*a* includes an aperture 92, while the tabular portion 88 of the second section 82*b* includes a post or peg 94 that is configured and dimensioned to snap into the aperture 92 with a friction fit.

As shown in FIG. 13, the first and second sections 82*a*, 82*b* are foldable toward each other along the hinge 84, so that the tabular sections 88 fold flat against each other, with the snap-together engagement between the peg 94 and its mating aperture 92 holding the two sections together. In this closed or folded configuration, the trough-like portions 86 together form a tubular sleeve 96 that is shaped and dimensioned to fit over and to conform to the exterior surface of the standard Y-site 62, of the type described above with reference to FIGS. 8, 10, and 11. Also, with the attachment 80 in its folded position, the cut-outs 90 form a substantially circular hole 98 that is dimensioned to receive the second inlet branch 63*b* of the Y-site or port 62, while the tabular portions 88 form an extension 100, on the outer surface of which a symbol 102 may be provided. Thus, the attachment 80 is placed over the Y-site or port 62, so that the second inlet branch 63*b* extends through the cut-outs 90, and the sections 82*a*, 82*b* are folded together along the hinge 84, and snapped together using the peg 94 and the mating aperture 92, whereby the attachment 80 is secured to the Y-site or port 62 with the second inlet branch 63*b* extending through the hole 98 formed by the cut-outs 90.

The method of using the second embodiment of the invention is the same as that described above for the first embodiment, except that the practitioner is provided with an IV line having a standard Y-site or port 62 and an appropriate snap-on attachment 60 or 80 for attachment to the Y-site or port 62. When an IV solution container 12 is selected, the drip chamber 14 is connected to it, and the first identification element is removed from the drip chamber and applied to the solution container. The third identification element (the attachment 60 or the attachment 80) is then attached to the Y-site or port 62 (as described above), the attachment 60 or 80 having an identification symbol 70 or 102 that matches the identification symbol on the first and second identification elements.

Figure 14:
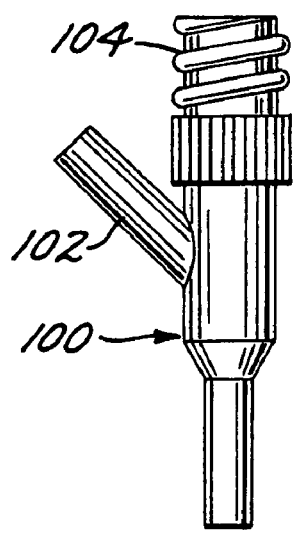
FIG. 14 is an elevational view of a prior art Luer-type Y-site or port.

FIG. 14 shows a prior art Luer-type Y-site or port 100, having a first inlet branch 102, and a second inlet branch 104 formed as a threaded Luer fitting 104. The Y-site or port 100 may typically have an internal valve (not shown) that is opened when a conduit having an appropriately configured and mating Luer fitting (not shown) is connected to the integral Luer fitting 104.

Figure 15:
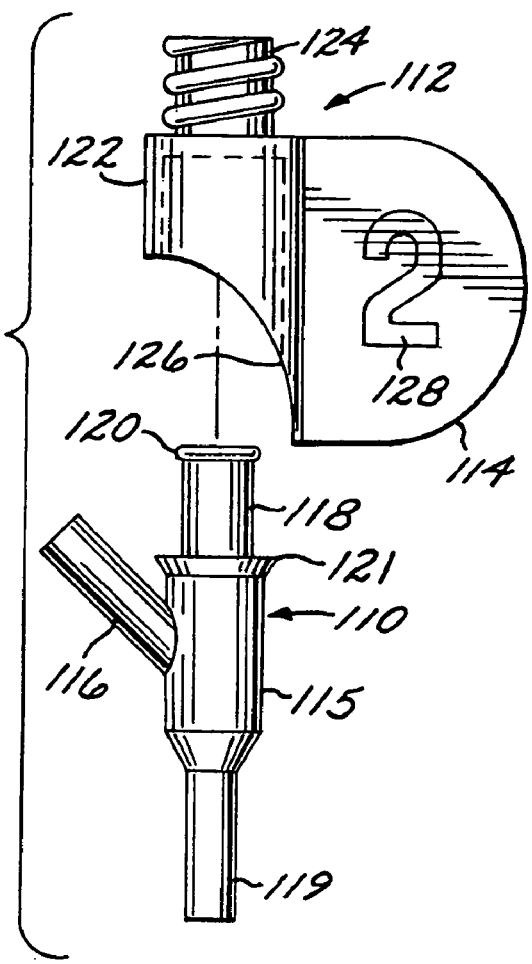
FIG. 15 is an exploded elevational view of an improved Luer-type Y-site or port having an attached identification element, in accordance with a third embodiment of the invention.
Figure 16:
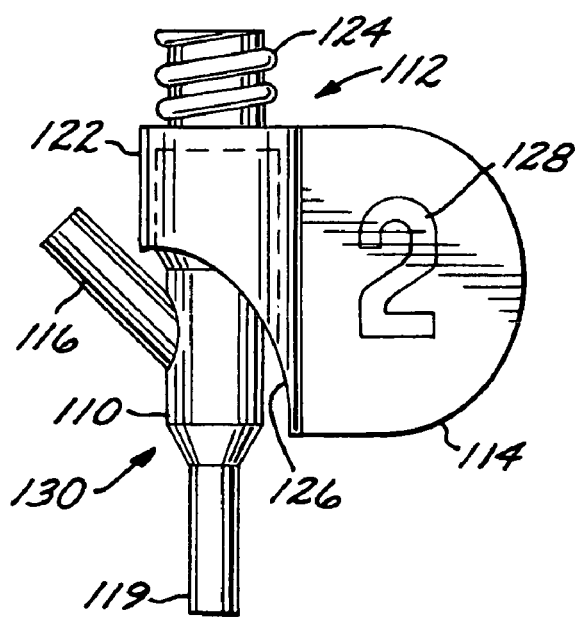
FIG. 16 is an elevational view of the Y-site or port of FIG. 15, showing the assembled Y-site or port.

FIGS. 15 and 16 show a Y-site or port 110, of the type described above with reference to FIG. 14, that has been modified, in accordance with a third embodiment of the invention, to include a permanently-attached connector member 112 having an integral identification element 114, formed as a flattened lateral extension, as described above in connection with the first embodiment. The Y-site or port 110 has a tubular main body 115 containing a valve (not shown), as described above; a first inlet branch 116; a second inlet branch 118; and an outlet branch 119. The second inlet branch 118 is configured as a hollow, tubular, substantially cylindrical member, preferably formed with a peripheral lip 120 around its open proximal end. The main body 115 advantageously has a peripheral rim 121 at its proximal end, at its juncture with the second inlet branch 118.

The connector member 112 comprises a tubular sleeve 122 having an inside diameter dimensioned to fit coaxially around the second inlet branch 118 and the rim 121 at the proximal end of the main body 115. Extending proximally from the sleeve 122 is a threaded Luer fitting 124. The sleeve 122 advantageously has a distally-extending portion 126, diametrically opposed to the first inlet branch 116, to which the identification element 114 is attached.

The connector member 112, comprising the sleeve 122, the Luer fitting 124, and the identification element 114 (which bears an identification symbol 128), is preferably formed as an integral unit. The connector member 112 is permanently fixed to the body 115 and or the second inlet branch 118 of the Y-site or port 110 by a suitable adhesive, or by other means, such as, for example, ultrasonic welding, to form an improved Luer-type Y-site or port 130 with an integral identification element 114, as shown in FIG. 16.

Figure 17:
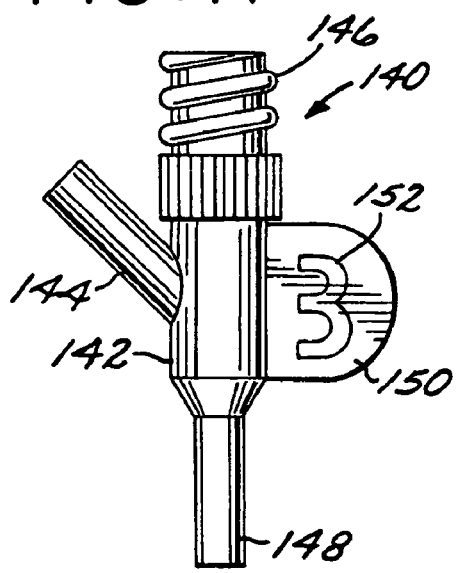
FIG. 17 is an elevational view of an improved Luer-type Y-site or port having an attached identification element, in accordance with a modification of the third embodiment of the invention.

FIG. 17 shows a Luer-type Y-site or port 140 in accordance with a modification or variation of the above-described embodiment of FIGS. 15 and 16. In accordance with this variation, the Y-site or port 140 is formed as an integral unit (e.g., by molding), comprising a hollow, tubular main portion or body 142, a first inlet branch 144, a second inlet branch 146, an outlet branch 148, and an identification element 150, with an identification symbol 152. The identification element is formed as a flattened extension that is integral with the body 142 and that extends laterally from it. The second inlet branch 146 is configured as a threaded Luer fitting. As in the devices described above with reference to FIGS. 14, 15, and 16, the body 142 may advantageously contain a valve that is opened by a mating Luer fitting.

FIGS. 18-27 illustrate another aspect of the invention, namely, an IV administration set identification kit comprising a plurality (e.g., four) IV identification element packages or packets 200a, 200b, 200c, 200d, each containing a matched set of three identification elements that are attachable to the components of an IV administration set. Specifically, as best shown in FIGS. 18-22, each of the packets 200a, 200b, 200c, 200d includes a transparent plastic envelope 202 sealed around its edges, with an openable side demarked by a tearable perforation 204 that defines a tear-away strip 206.

Each of the packets 200a, 200b, 200c, 200d contains a different matched set of three identification elements. For example, the first packet 200a contains a first set of first, second, and third identification elements 208a, 210a, 212a, respectively, that are marked with a first identification symbol, e.g., the numeral "1." Likewise, the second packet 200b contains a second set of first, second, and third identification elements 208b, 210b, 212b, respectively, that are marked with a second identification symbol, e.g., the numeral "2." The third packet 200c contains a third set of first, second, and third identification elements 208c, 210c, 212c, respectively, that are marked with a third identification symbol, e.g., the numeral "3." Finally, the fourth packet 200d contains a fourth set of first, second, and third identification elements 208d, 210d, and 212d, respectively, that are marked with a fourth identification symbol, e.g., the numeral "4." Preferably, the identification elements in each packet also bear a distinctive and different color. The packets can be provided in a set of four as shown, with four distinct identification indicia or symbols, or in sets of different numbers of packets, wherein the identification elements in each packet in the set bear a unique identification symbol.

Figures 23, 24, 25, 26:
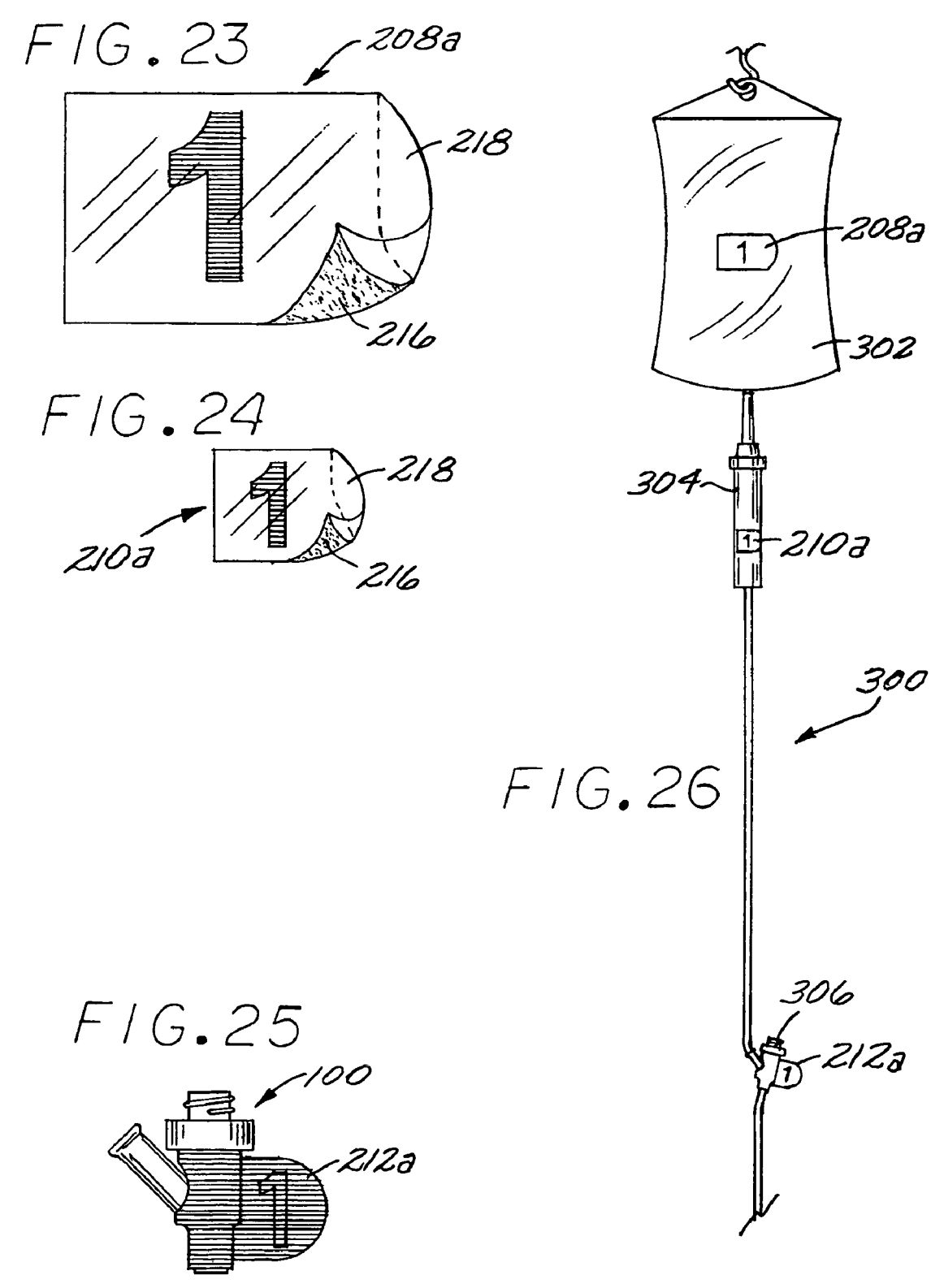

The first and second identification elements 208a, 208b, 208c, 208d; and 210a, 210b, 210c, 210d are preferably in the form of the adhesive strips or patches described above. They are advantageously carried, while contained in the packets 200a, 200b, 200c, 200d on a flexible carrier sheet or backing sheet 214, to which they removably adhere by means of an adhesive backing 216, as shown in FIGS. 23 and 24. The first and second identifications elements contained in the packets 200a, 200b, 200c, 200d differ from the first and second identification elements described above in that those contained in the packets each have a short pull tab or extension 218 that is not backed with an adhesive, thereby facilitating the removal of these identification elements from their respective backing sheets 214.

The third identification elements 212a, 212b, 212c, 212d are preferably of the type described above with reference to FIGS. 9-11, and designated therein by the numeral 60, although any of the other removable Y-site or port identification elements described herein may be used. As shown in FIG. 25, the Y-site or port 100 of FIG. 14 is shown with the third identification element 212a from the packet 200a attached to it.

The first, second, and third identification elements may be removed from their packet when it is desired to mark or identify the components of an IV administration set. The first and second identification elements are removed from the backing sheet 214 and adhesively attached to the IV solution container and the drip chamber, respectively; and the third identification element is attached to the Y-site. Thus, for example, FIG. 26 shows an IV administration set 300 to which the identification elements of the first packet 200a have been attached. Specifically, an IV solution container 302 is marked with the first identification element 208a, a drip chamber 304 is marked with the second identification element 210a, and a Y-site or port 306 is marked with the third identification element 212a.

While preferred embodiments of the invention have been described herein, it will be appreciated that a number of variations and modifications will suggest themselves to those skilled in the pertinent arts. These variations and modifications are considered within the spirit and scope of the invention, as defined in the claims that follow.

What is claimed is:

1. An IV administration set identification kit for identifying an IV administration set having an IV solution container, a drip chamber, and an IV line including a Y-site or port, the kit comprising:
   an openable packet containing first, second, and third identification elements having matching identification symbols, wherein the first identification element is configured for attachment to the container, the second identification element is configured for attachment to the drip chamber, and the third identification element is configured for attachment to the Y-site, further wherein the third identification element comprises a sleeve with an axial slit and an extension marked with an identification symbol, and further wherein the sleeve is shaped and dimensioned to fit over and to conform to the exterior surface of the Y-site.

2. The IV administration set identification kit of claim 1, wherein the first and second identification elements are adhesive strips.

3. The IV administration set identification kit of claim 1, wherein the first and second identification elements are removably attached to at least one flexible backing sheet.

4. An IV administration set identification kit for identifying an IV administration set having an IV solution container, a drip chamber and an IV line including a Y-site or port, the kit comprising a packet with an openable side, wherein the packet contains:
   a first adhesive strip configured for attachment to the IV solution container;
   a second adhesive strip configured for attachment to the drip chamber; and
   a Y-site identification element configured for attachment to the Y-site;
   wherein the first and second adhesive strips and the Y-site identification element are marked with matching identification symbols, further wherein the Y-site identification element comprises a sleeve with an axial slit and an extension marked with an identification symbol, and further wherein the sleeve is shaped and dimensioned to fit over and to conform to the exterior surface of the Y-site.

5. The IV administration set identification kit of claim 4, wherein the first and second adhesive strips are removably attached to at least one flexible backing sheet.

* * * * *